(12) United States Patent
Lobel et al.

(10) Patent No.: US 9,434,959 B2
(45) Date of Patent: *Sep. 6, 2016

(54) VIRUS-LIKE PARTICLES FOR TREATMENT OF VIRAL INFECTIONS

(71) Applicant: BEN GURION UNIVERSITY OF THE NEGEV RESEARCH AND DEVELOPMENT AUTHORITY, Beer Sheva (IL)

(72) Inventors: Leslie Lobel, Omer (IL); Guy Gubi, Rehovot (IL)

(73) Assignee: BEN GURION UNIVERSITY OF THE NEGEV RESEARCH AND DEVELOPMENT AUTHORITY, Beer Sheva (IL)

( * ) Notice: Subject to any disclaimer, the term of this patent is extended or adjusted under 35 U.S.C. 154(b) by 28 days.

This patent is subject to a terminal disclaimer.

(21) Appl. No.: 14/249,864

(22) Filed: Apr. 10, 2014

(65) Prior Publication Data

US 2014/0213640 A1 Jul. 31, 2014

Related U.S. Application Data

(63) Continuation of application No. 13/440,350, filed on Apr. 5, 2012, now abandoned, which is a continuation-in-part of application No. 12/304,994, filed as application No. PCT/IL2007/000720 on Jun. 14, 2007, now Pat. No. 8,153,115.

(60) Provisional application No. 60/813,733, filed on Jun. 15, 2006.

(51) Int. Cl.

| | |
|---|---|
| *A01N 63/00* | (2006.01) |
| *A61K 38/00* | (2006.01) |
| *A61K 39/395* | (2006.01) |
| *C07H 21/04* | (2006.01) |
| *C07K 1/00* | (2006.01) |
| *C12N 15/86* | (2006.01) |
| *A61K 39/145* | (2006.01) |
| *C07K 14/005* | (2006.01) |
| *C07K 16/10* | (2006.01) |
| *C12N 7/00* | (2006.01) |
| *A61K 39/12* | (2006.01) |
| *C12N 7/02* | (2006.01) |
| *C12N 7/04* | (2006.01) |
| *A61K 39/00* | (2006.01) |

(52) U.S. Cl.
CPC .............. *C12N 15/86* (2013.01); *A61K 39/12* (2013.01); *A61K 39/145* (2013.01); *C07K 14/005* (2013.01); *C07K 16/1018* (2013.01); *C12N 7/00* (2013.01); *A61K 2039/5258* (2013.01); *C07H 21/04* (2013.01); *C07K 2317/622* (2013.01); *C07K 2317/80* (2013.01); *C12N 7/02* (2013.01); *C12N 7/045* (2013.01); *C12N 2760/14134* (2013.01); *C12N 2760/16122* (2013.01); *C12N 2760/16123* (2013.01); *C12N 2760/16143* (2013.01)

(58) Field of Classification Search
CPC .................. A61K 39/145; A61K 2039/5258; C07K 14/005; C07K 16/1018; C07K 2317/622; C07K 2317/80; C07H 21/04; C12N 7/02; C12N 7/045; C12N 2760/16122; C12N 2760/16123
USPC .................... 424/93.2, 93.6, 135.1; 530/300; 536/23.72, 24.1

See application file for complete search history.

(56) References Cited

U.S. PATENT DOCUMENTS

| | | |
|---|---|---|
| 6,387,662 B1 | 5/2002 | Liang et al. |
| 2003/0232325 A1 | 12/2003 | Palese et al. |
| 2005/0037487 A1 | 2/2005 | Kawaoka et al. |
| 2005/0186621 A1 | 8/2005 | Galaza et al. |
| 2008/0089862 A1 | 4/2008 | Benhar et al. |
| 2008/0131912 A1 | 6/2008 | Tu et al. |

FOREIGN PATENT DOCUMENTS

WO 01/60849 A2 8/2001

OTHER PUBLICATIONS

Kawaoka et al., 2005, US 20050037487 A1.*
D. Zamarin, et al., "Influenza Virus PB1-F2 Protein Induces Cell Death through Mitochondrial ANT3 and VDAC1", PLOS Pathogens, Sep. 2005, p. 0040-0054, vol. 1, Issue 1.
Zhang et al., Clinical and Diagnostic Laboratory Immunology, vol. 7, No. 1, p. 58-63 (2000).
Bai et al., 2004, Xi Bao Yu Fen Zi Mian Yi Xue Za Zhi (Chinese Journal of Cellular and Molecular Immunology), vol. 20, No. 6, pp. 705-707, abstract only.
Kawaoka, Y. 2001, computer printout pp. 8-9, SEQ ID No. 3.
Barber et al., 1997, computer printout pp. 4-5, SEQ ID No. 4.
Kaji, A, 1995, computer printout p. 4, SEQ ID No. 5.
Kawaoka et al., 2000, computer printout pp. 5-6, SEQ ID No. 6.
Dowling et al., 2001, Geneseq Accession No. AAE09031, computer printout pp. 5-6.

* cited by examiner

*Primary Examiner* — Shin Lin Chen
(74) *Attorney, Agent, or Firm* — Browdy and Neimark, PLLC

(57) ABSTRACT

The invention provides virus-like particles for treatment of viral infections based on the virus causing the infection. The virus-like particles comprise the virus recombinant proteins that form a capsid, recombinant virus membrane proteins attached to the capsid and vRNA packaged within said capsid. The vRNA is generated from a DNA sequence encoding a polypeptide capable of specifically binding to a constant region of a nonstructural protein of the virus that is essential for propagation of the virus.

18 Claims, 4 Drawing Sheets

Fig. 2A

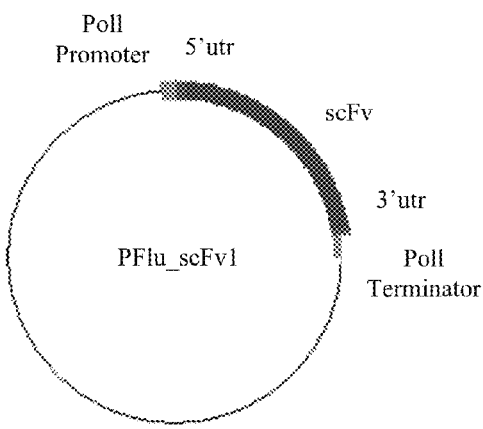

Fig. 2B

Sequences:
PolI promotor: GGGTTATT (SEQ ID NO: 3)
5' UTR: AGTAGAAACAAGGGTATTTTTCT (SEQ ID NO: 4)
scFv:
GAGCTGCAGCTGTTGGAGTCTGGGGGAGGCTTGGTACAGCCTGGGGGGTCCCTGAGACTCTCCTGTGCAGCCT
CTGGATTCACCTTTAGCAGCTATGCCATGAGCTGGGTCCGCCAGGCTCCAGGTAAGGGGCTGGAGTGGGTTTC
AGCTATTAGTGGTAGTGGTGGTAGCACATACTACGCAGACTCCGTGAAGGGCCGGTTCACCATCTCCAGAGA
CAATTCCAAGAACACGCTGTATCTGCAAATGAACAGCCTGAGAGCCGAGGACACGGCCGTATATTACTGTGC
AAGACTGACTAGGACCATTCAGCCCTCAGGGGCCAGGGCACCCTGGTCACCGTCTCTTCAGATATCCTGACGC
AGTCTCCAGGCACCCTGTCTTTGTCTCCAGGGGAAAGAGCCACCCTCTCCTGCCTGCTCGTATCACGGGGGCA
GAGGATCCAGCTGCCACCCTGAACCTGGTACCAGCAGAAACCTGGCCAGGCTCCCAGGCTCCTCATCTATCTC
CTCAAAGCCTCCAGTCGGGGGAAGCGAGACCTCTATGACAGGTTCAGTGGCAGTGGGTCTGGGACAGACTTC
ACTCTCACCATCAGCAGACTGGAGCCTGAAGATTTTGCAGTTTATTACTGTTGGTACTATAATCGCGGGACCA
AACTGGATATCAAAGCGGCCGCAGGTGGCGCAGATATCGTGCTGACTCAGCCACCCTCAGCGTCTGGGACCC
CCGGGCAGAGGGTCACCATCTCTTGTACTTCATATTGTACCGATGAGTCCTTCCGAATAAAAGGATGGTACCA
GCAGCTTGCAGGAAAAGCTCCCAAACTCCTCATTTATACCAGTCTGCTCGAGGGGGTCTCTGACCGATTCTCT
GGCTCCAAGTCTGGCACCTCAGCCTCCCTGGCCATCAGTGGGCTCCGGTCCGAGGATGAGGCTGATTATTACT
GTCGGCCCACCCAGCTCGGTACCCAGCTCACCGTCCTAGCGGCCGCAGGTGGCGCA (SEQ ID NO: 2)
3' UTR: GATGTCACTCAGTGAGTGATTATCTACCCTGTTTCTACT (SEQ ID NO: 6)
PolI terminator: CCCCCC (SEQ ID NO: 5)

SEQUENCE LISTING

<160> NUMBER OF SEQ ID NOS: 7

<210> SEQ ID NO 1
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 25 AA PB1 PEPTIDE

<400> SEQUENCE: 1

Met Asp Val Asn Pro Thr Leu Leu Phe Leu Lys Val Pro Ala Gln Asn
1               5                   10                  15

Ala Ile Ser Thr Thr Phe Pro Tyr Thr
            20                  25

<210> SEQ ID NO 2
<211> LENGTH: 1001
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: scFv

<400> SEQUENCE: 2
gagctgcagc tgttggagtc tgggggaggc ttggtacagc ctgggggtc cctgagactc        60 tcctgtgcag cctctggatt caccttagc agctatgcca tgagctgggt ccgccaggct       120
ccaggtaagg gctggagtg gtttcagct attagtggta gtggtggtag cacatactac       180
gcagactccg tgaagggccg gttcaccatc tccagagaca attccaagaa cacgctgtat       240
ctgcaaatga acagcctgag agccgaggac acggccgtat attactgtgc aagactgact       300
aggaccattc agccctcagg ggccagggca ccctggtcac cgtctcttca gatatcctga       360
cgcagtctcc aggcaccctg tctttgtctc caggggaaag agccaccctc tcctgcctgc       420
tcgtatcacg ggggcagagg atccagctgc caccctgaac ctggtaccag cagaaacctg       480
gccaggctcc caggctcctc atctatctcc tcaaagcctc cagtcggggg aagcgagacc       540
tctatgacag gttcagtggc agtgggtctg gacagactt cactctcacc atcagcagac       600
tggagcctga agatttttgca gtttattact gttggtacta taatcgcggg accaaactgg       660
atatcaaagc ggccgcaggt ggcgcagata tcgtgctgac tcagccaccc tcagcgtctg       720
ggacccccgg gcagagggtc accatctctt gtacttcata ttgtaccgat gagtccttcc       780
gaataaaagg atggtaccag cagcttgcag gaaaagctcc caaactcctc atttatacca       840
gtctgctcga gggggtctct gaccgattct ctggctccaa gtctggcacc tcagcctccc       900
tggccatcag tgggctccgg tccgaggatg aggctgatta ttactgtcgg cccacccagc       960
tcggtaccca gctcaccgtc ctagcggccg caggtggcgc a                         1001

<210> SEQ ID NO 3
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: RNA Pol I promoter

```
<400> SEQUENCE: 3 gggttatt                                                                    8

<210> SEQ ID NO 4
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' URT

<400> SEQUENCE: 4
agtagaaaca agggtatttt tct                                                  23

<210> SEQ ID NO 5
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: RNA POL 1 TERMINATOR

<400> SEQUENCE: 5 cccccc                                                                      6

<210> SEQ ID NO 6
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3' UTR

<400> SEQUENCE: 6
gatgtcactc agtgagtgat tatctaccct gtttctact                                 39

<210> SEQ ID NO 7
<211> LENGTH: 48
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 48 AA PB1 PEPTIDE

<400> SEQUENCE: 7

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Tyr Ser His
            20                  25                  30

Gly Thr Gly Thr Gly Tyr Thr Met Asp Thr Val Asn Arg Thr His Gln
        35                  40                  45
```

VIRUS-LIKE PARTICLES FOR TREATMENT OF VIRAL INFECTIONS

FIELD OF THE INVENTION

The invention relates to virus-like particles for treatment of viral infections based on the virus causing the infection. The virus-like particles comprise the virus recombinant proteins that form a capsid, recombinant virus membrane proteins attached to the capsid and vRNA packaged within said capsid. The invention further relates to a DNA sequence encoding a polypeptide capable of specifically binding to a constant region of a nonstructural protein of the virus that is essential for propagation of the virus, and to methods for producing said virus-like particles and for treating viral infections.

BACKGROUND OF THE INVENTION

Viruses lack the cellular machinery for self-reproduction. The viral genome codes for the proteins that constitute the protective outer shell (capsid) as well as for those proteins required for viral reproduction that are not provided by the host cell. The capsid consists of monomeric subunits of protein and serves to protect the virus's genetic material, detect cells suitable for infection, and initiate the infection by "opening" the target cell to inject DNA into the cytoplasm. After entering the cell, the virus's genetic material begins the destructive process of causing the cell to produce new viruses.

Viruses are classified as either DNA or RNA virus according to the nucleic acid type of their genetic material. The RNA viruses are divided into three groups: Group III—viruses possessing double-stranded RNA genomes, e.g. rotavirus; Group IV—viruses possessing positive-sense single-stranded RNA genomes including for example Hepatitis A virus, enteroviruses, rhinoviruses, poliovirus, foot-and-mouth virus, SARS virus, hepatitis C virus, yellow fever virus, and rubella virus; and Group V—viruses possessing negative-sense single-stranded RNA genomes inclusing, for example, the deadly Ebola and Marburg viruses, and the influenza, measles, mumps and rabies virus. Some negative sense RNA viruses contain also positive sense RNA and are referred to as ambisense viruses (e.g. some bunyaviruses).

The influenza virus is an RNA virus of the family Orthomyxoviridae, which comprises the influenzaviruses, isavirus, and thogotovirus. There are three types of influenza virus: Influenzavirus A, Influenzavirus B, or Influenzavirus C. Influenza A and C viruses infect multiple species, while influenza B virus infects almost exclusively humans.

Influenzavirus A has only one soecies, called the Influenza A virus. It is hosted by birds, but may also infect several species of mammals. Unusually for a virus, the influenza A virus genome is not a single piece of nucleic acid; instead, it contains eight pieces of segmented negative-sense RNA (13.5 kilobases total), which encode 11 proteins.

The influenza virus binds specifically to sialic acid sugars present on the surface of certain cells through the specific receptor hemagglutinin and is taken up through endocytosis into the cell, where the viral RNA (vRNA) is transported into the nucleus. The vRNA is then either exported back into the cytoplasm and translated, or remains in the nucleus, where it is transcribed into new vRNA molecules by RNA-dependent RNA polymerase (RDRP). Newly-synthesised viral proteins are either secreted through the Golgi apparatus onto the cell surface (in the case of neuraminidase and hemagglutinin) or transported back into the nucleus where some form the capsid shell and others bind vRNA that is packaged within the capsid to form new viral genome particles comprising the negative-sense vRNAs, RDRP and other viral proteins.

The newly formed viral particles leave the host cells by entering into plasma membrane protusion with clustered hemagglutinin and neuraminidase molecules. The mature virus then buds off from the cell in a sphere of host phospholipid membrane, acquiring hemagglutinin and neuraminidase with this membrane coat. Similarly to the stage of entry into the cell, the viruses adhere to the cell through hemagglutinin; the mature viruses then detach once the neuraminidase has cleaved sialic acid residues from the host cell. After the release of new influenza virus, the host cell dies.

The RNA-dependent RNA transcriptase lacks RNA proofreading activity and therefore mistakes introduced into the copied polynucleotide are not corrected. The frequency of errors is roughly a single nucleotide insertion error for every 10 thousand nucleotides, which is the approximate length of the influenza vRNA. Hence, nearly every newly produced influenza virus particle has a vRNA sequence that is different from other influenza virus particles. The separation of the genome into eight separate segments of vRNA allows mixing or reassortment of vRNAs, if more than one viral line has infected a single cell. The resulting rapid change in viral genetics produces antigenic shifts and allows the virus to infect new host species and quickly overcome protective immunity For a compound intended to inhibit a process essential for viral propagation to be effective over time, it should therefore target constant regions of the target proteins and not—as is the case with current vaccines—target viral cell surface proteins that rapidly change their antigenicity.

There are two different replication processes for viruses containing RNA. In the first process, the viral RNA is directly copied using RDRP. In influenza virus, this complex consists of three polypeptides—PB1, PB2, and PA—collectively referred to as P proteins, while in other RNA viruses RDRP consists of a single polypeptide. The P protein complexes are normally associated with viral nucleocapsids, consisting of genomic RNA (vRNA) molecules covered with viral nucleoprotein. PB 1 is the best characterized of the three P proteins; it contains five sequence blocks common to all RNA-dependent RNA polymerases and RNA-dependent DNA polymerases. PB2 has cap-binding and endonucleolytic activities which are necessary for viral mRNA synthesis. PA is indispensable for proper plus-strand copy RNA and vRNA synthesis, but no specific function in these processes has been assigned to it. Bipartite nuclear localization signals have been found in each of the three P proteins. Inside the nucleus, the RDRP enzyme uses the vRNA copy as a template to make hundreds of duplicates of the original RNA.

One representative of the RNA positive sense viruses is human hepatitis C virus. The positive sense RNA genome is directly translated into viral proteins without intermediate steps.

The most effective medical approaches to viral diseases thus far are vaccination to provide resistance to infection, and drugs that inhibit the viral proteins such as the cocktail of inhibitors used to treat human immunodeficiency virus (HW)-AIDS. These drugs act on three critical step during the HIV cycle, i.e. replication, production of infectious viral particles; and fusion with the cellular membrane, thereby blocking entry into the host cell. A fourth step that may be interfered with is the budding, or release of the mature viral particles from the host cell. The three stages: replication, packaging and fusion with the cell membrane (for entry or release of viral particles), are the main essential processes in the viral propagation cycle amenable to manipulation with specific compounds for all enveloped viruses—whether positive or negative sense viruses.

Passive immunization with specific antiviral monoclonal or polyclonal antibodies has also proven effective both as prophylactic and therapeutic antiviral agents, e.g. in the case of human polyclonal antibodies against West Nile Virus or the monoclonal antibody Palivizumab approved for prevention and treatment of infection caused by respiratory syncitial virus.

Antibodies are made up of two identical heavy and two identical light chains Each antibody has a constant region, which is the same for all immunoglobulins of the same class, and a variable region, which differs between immunoglobulins of different B cells, but is the same for all immunoglobulins produced by the same B cell. The variable regions of the heavy and light chains can be fused together to form a single chain variable fragment (scFv), which retains the original specificity of the parent immunoglobulin. "Designed" monoclonal antibody therapy is already being employed in a number of diseases and in some forms of cancer. Trastuzumab (Herceptin®, Genethech), a humanized monoclonal antibody that acts on the HER2/neu (erbB2) receptor, is1 used in breast cancer therapy in patients with tumors overexpressing the HER2/neu receptor.

Virotherapy has been designed as a promising strategy for treatment of various diseases, especially cancer. It consists in the use of viruses by reprogramming viruses to only attack cancerous cells while healthy cells remained undamaged. The viruses are used most commonly as a vector directed to specifically target cells and DNA in particular.

SUMMARY OF THE INVENTION

In one aspect the present invention provides a DNA sequence encoding a polypeptide capable of specifically binding to a constant region of a virus nonstructural protein that is essential for propagation of a virus, whereby the binding interferes with the activity of said nonstructural viral protein and inhibits the propagation of said virus.

In another aspect, the invention provides a plasmid comprising said DNA sequence, that may be operably linked to an RNA polymerase promoter, such as a human RNA polymerase I promoter, and flanked by a transcription terminator and viral transcription and packaging signal sequences.

In a further aspect, the invention provides a virus-like particle that contains recombinant virus proteins that form a capsid, recombinant virus membrane proteins attached to the surface of the capsid and vRNA packaged within said capsid, wherein said vRNA is generated by intracellular transcription of a DNA sequence as defined herein.

In yet a further aspect, the invention provides a method for producing a virus-like particle of the invention.

In an additional aspect, the instant invention relates to a pharmaceutical composition comprising a virus-like particle as defined herein and a pharmaceutically acceptable carrier, particularly for the treatment or prevention of a viral infection caused by the virus on which the virus-like is based.

In still a further aspect, the invention relates to a method of treating a viral infection, comprising administering to a subject infected with a virus an effective amount of a virus-like particle based on the virus causing the infection or a pharmaceutical composition comprising it.

BRIEF DESCRIPTION OF THE FIGURES

FIGS. 2A-2B show the plasmid comprising the scFv cDNA of SEQ ID NO:2 (FIG. 2A) and the nucleotide sequences of the RNA polymerase I promoter (Pol1 promoter, SEQ ID NO:3), 5' untranslated region (UTR, SEQ ID NO:4), 3'UTR (SEQ ID NO:6), and Pol1 terminator (SEQ ID NO:5) comprised within the plasmid (FIG. 2B).

DETAILED DESCRIPTION OF THE INVENTION

Figure 1:
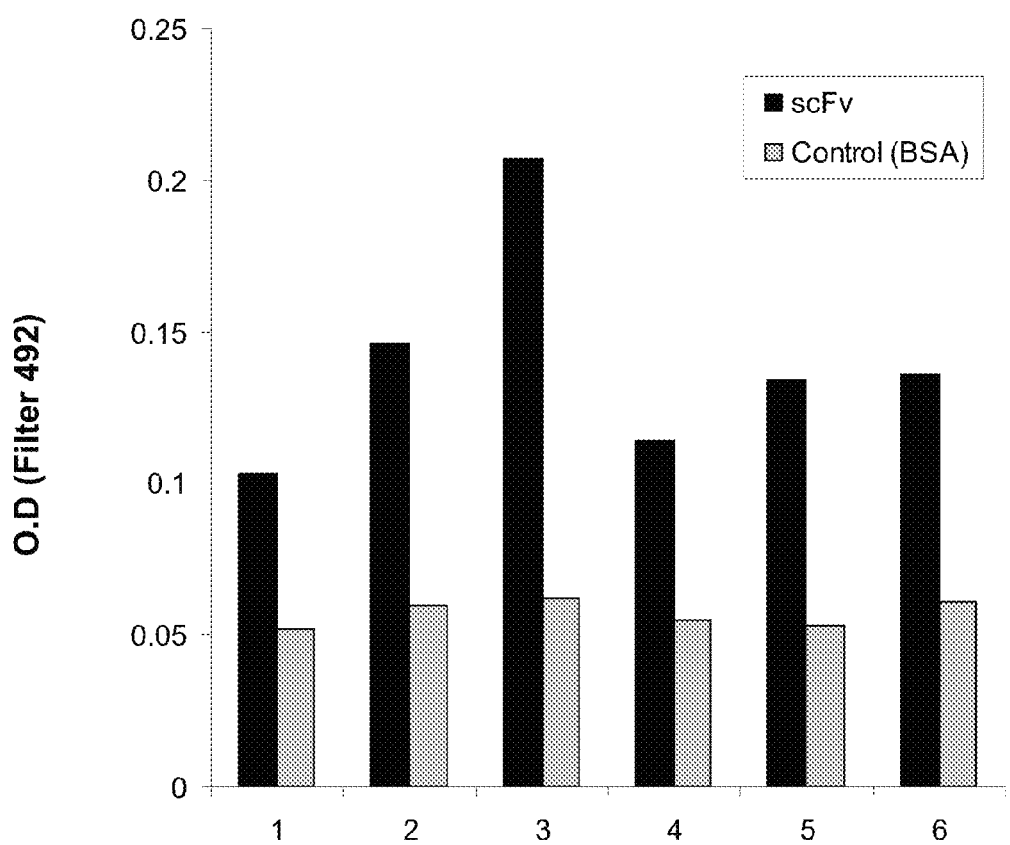
FIG. 1 shows specific binding of scFv-phages to the 25-mer N-terminus peptide of SEQ ID NO: 1 of the PB1 subunit of the RDRP of influenza A virus, bound to streptavidin-coated magnetic beads.

As described in the Background section, virotherapy has been proposed for treatment of diseases, particularly cancer.

The present invention is based on the concept that an infection caused by a naturally occurring (wild type) virus may be treated or prevented by infecting the subject with a viral vector or virus-like particle, based on the same naturally occurring virus, but designed in a way that it is not pathogenic but rather inhibits the virus causing the infection. This feature, that the virus-like particle is based on the naturally occurring virus, ensures that the virus-like particle infects cells with the same or similar specificity as the naturally occurring virus and thus only relevant tissue is affected by the virus-like particle.

The virus-like particle of the invention contains a DNA sequence encoding for a polypeptide targeting viral proteins or viral replication associated host proteins; thus the DNA product, also referred to herein as polypeptide inhibitor, having been expressed in said cell infected by a virus, specifically binds to, and interferes with the activity of the target protein and consequently inhibits the propagation of the virus.

As used herein, the term "polypeptide" refers both to a peptide or polypeptide of any length, but comprising at least 25 amino acids.

In one aspect, the invention relates to a DNA sequence encoding a polypeptide capable of specifically binding to a constant region of a virus nonstructural protein that is essential for propagation of a virus, whereby the binding interferes with the activity of said nonstructural viral protein and inhibits the propagation of said virus.

Although the invention is applicable to any virus family or group, it is in particular directed to the groups of RNA negative sense viruses, RNA ambisense viruses and RNA positive sense viruses, particularly the orthomyxoviridae, paramyxoviridae, filoviridae, rhabdovirida, arenaviridae, bunyaviridae and flaviviridae virus families. Among these families the viruses causing infections that are especially amenable to treatment or prevention according to the invention are the orthomyxoviridae influenza virus, the paramyxoviridae human respiratory syncytial virus, the filoviridae ebola and Marburg viruses, the rhabdovirida rabies virus, the arenaviridae lassa virus, the bunyaviridae hanta virus and the flaviviridae hepatitis C virus. In one embodiment, the virus is an influenza virus, in particular, influenza A virus.

The nonstructural viral proteins amenable to interference of their activity and inhibition of the propagation of a virus may be selected from:
(a) influenza virus: the PB1, PB2, or PA subunit of the RNA dependent RNA polymerase (RDRP), the nucleoprotein (NP), and the M proteins;
(b) human respiratory syncytial virus: the NP and RDRP proteins;
(c) ebola or Marburg virus: the L, VP35, NP, and VP30 proteins;
(d) rabies virus: the NP and RDRP proteins;
(e) lassa virus: the L (RDRP) and N (Nucleoprotein) proteins;
(f) hanta virus: the L (RDRP) and N (Nucleoprotein) proteins; and
(g) hepatitis C virus: the NS2, NS3 and NS5 (RDRP) proteins.

In certain embodiments, the nonstructural viral protein is an influenza A virus protein as defined in (a) above.

As previously mentioned, the viral propagation cycle involves several steps. First, the virus attaches to specific host cells through receptors specific for certain cell surface antigens. For example, the influenza A virus envelop protein hemagglutinin (HA) specifically binds to cells displaying sialic acid on their surface. The virus is taken up through endocytosis and the genomic material is released inside the host cell. The next critical step is the replication of the viral genome and expression of viral proteins, followed by assembly of the capsid, the outer shell comprising a number of viral proteins. The newly replicated viral genome, often associated with nucleoproteins, is packaged within the capsid. The mature virus comprising the capsid and the genomic material exit the host cell by budding off from the cell in a sphere of host phospholipid membrane, acquiring the viral membrane proteins hemagglutinin and neuraminidase with this membrane. The term "budding" is used herein to describe this last stage of viral propagation.

The nonstructural protein is involved in a cellular process that is essential for propagation of the virus. This cellular process may be selected from replication of the viral genetic material, packaging of said genetic material into the viral capsid or budding of the capsid from the host cell.

It has been found in accordance with the present invention that influenza A viral like particles expressing a PB1 peptide or an scFv specific for a PB1 peptide, which were generated from cloned cDNA, are capable of inhibiting wild type influenza A viral replication in human cells.

Thus, in some embodiments, the virus is influenza A virus, the cellular process is replication of the viral genetic material, and the nonstructural viral protein is the PB1 subunit of influenza A virus RDRP.

In one embodiment, the polypeptide inhibitor is a single chain variable fragment antibody (scFv) polypeptide, capable of specifically binding to the PA binding domain of the PB1 subunit of the influenza A RDRP.

In certain embodiments, the scFv polypeptide specifically binds to the N-terminus 25-amino acid sequence of PB1 of SEQ ID NO:1; in particular, this scFv is encoded by the DNA sequence of SEQ ID NO:2. Such a peptide interferes with the interaction between the PB1 and PA subunits of the influenza A virus RDRP, inhibits transcription of vRNA and thereby inhibits influenza A virus replication.

In another embodiment, the polypeptide inhibitor is a polypeptide comprising a sequence of the PB1 subunit capable of binding to the PB1 binding domain of the PA subunit represented by SEQ ID NO: 1 or SEQ ID NO: 7. The invention contemplates the possibility of the DNA sequences encoding for multiple copies of the polypeptide inhibitor. For example, the DNA sequence may comprise 2, 3, 4, 5, 6, 7, 8, 9, 10, or more copies of the nucleotide sequence encoding for the polypeptide inhibitor. Each copy may be operably linked to a promoter and flanked by a terminator (see below) or the copies may be separated by nucleotide sequences encoding recognition sites for nucleases that produce RNA fragments that each encode for one polypeptide inhibitor, or recognition sites for proteases that cleave the polypeptide product into multiple copies of the desired inhibitor.

The invention further relates to a plasmid comprising a DNA sequence as defined herein. In one embodiment, the DNA sequence in the plasmid is operably linked to an RNA polymerase promoter, such as a RNA polymerase I promoter, a T3 RNA polymerase promoter or a T7 RNA polymerase promoter, and is flanked by an RNA polymerase transcription terminator, e.g. an RNA polymerase I transcription terminator, a T3 RNA polymerase transcription terminator or a T7 RNA transcription terminator sequence and by viral transcription and packaging signal sequences.

In particular, the RNA polymerase promoter is a human RNA polymerase I promoter represented by SEQ ID NO: 3, the RNA polymerase transcription terminator sequence is the human RNA polymerase I transcription terminator sequence of SEQ ID NO: 5 and said viral transcription and packaging signal sequences are 3' and 5' UTR sequences represented by SEQ ID NO: 4 and SEQ ID NO: 6.

In another aspect, the instant invention relates to a virus-like particle adapted for treating a viral infection, wherein said virus-like particle is based on an infecting virus causing the viral infection, and said virus-like particle comprises: recombinant viral proteins which are of the same species as said infecting virus and form a capsid, recombinant viral membrane proteins which are of the same species as said infecting virus and are attached to the surface of said capsid, and vRNA packaged within said capsid, wherein said vRNA is generated by intracellular transcription of a DNA sequence encoding a polypeptide capable of specifically binding to a constant region of a nonstructural protein of said infecting virus, said nonstructural protein being essential for propagation of said infecting virus, whereby said binding interferes with the activity of said nonstructural viral protein and inhibits the propagation of said virus.

The term "virus-like particle" as defined herein means also a "viral vector". According to the invention, the viral vector is identical to the wild-type virus, but instead of containing all the genetic material of the wild-type virus, it contains a nucleotide sequence that expresses a polypeptide targeting viral proteins or viral replication's associated host proteins. An example of such a nucleotide sequence packaged within the particle is one that encodes for an scFv against viral proteins or against viral replication's associated host proteins, as shown herein for the scFv isolated from a library of scFvs against influenza virus. Another example is a nucleotide sequence that encodes for a peptide or oligopeptide that is substantially identical to a fraction of an endogenous viral polypeptide and is therefore capable of competing with the endogenous viral polypeptide for a crucial interaction with another viral protein, such as in the case of PA and PB 1. For example, the competing oligopeptide may be the 25 amino acid long PB1 N-terminus amino acid sequence of SEQ ID NO: 1. This oligopeptide, in contrast to the full native PB 1 polypeptide, will interrupt the interaction between PA and PB 1 and therefore will inhibit viral propagation.

The recombinant proteins that form the capsid and the recombinant virus membrane proteins attached to the surface of the capsid must be of the same virus that is to be inhibited. Thus, for treating influenza virus infection, the nonstructural proteins that form the capsid are the PB1, PB2, or PA subunit of the RDRP of influenza virus, or the NP or the M protein of the influenza virus, and the virus membrane proteins attached to the surface of the capsid are hemagglutinin and neuraminidase.

In a certain embodiment, the virus-like particle is an influenza A virus-like particle.

In other embodiments, nonstructural protein of the virus-like particle is selected from the group consisting of the PB1, PB2, and PA subunits of the RNA dependent RNA polymerase (RDRP), the nucleoprotein (NP), and the M protein of influenza virus.

In certain embodiments, the virus-like particle of the present invention may comprise the membrane proteins hemagglutinin and neuraminidase, and the vRNA may be generated by intracellular transcription of the DNA sequence of an scFv. In particular, the scFv polypeptide is capable of specifically binding to the PA binding domain of the PB1 subunit of the influenza A virus RDRP. As exemplified herein below, but not limited by it, the scFv polypeptide may specifically bind to the PB 1 N-terminus amino acid sequence of SEQ ID NO: 1, and in certain embodiments the scFv is encoded by a DNA sequence represented by SEQ ID NO: 2. Alternatively, and also exemplified herein below, the polypeptide comprising a sequence of the PB1 subunit capable of binding to the PB1 binding domain of the PA subunit is represented by SEQ ID NO: 1.

In still another aspect, the instant invention relates to a method for producing a virus-like particle as defined above, comprising introducing into an eukaryotic host cell:

(i) a plasmid comprising a DNA sequence encoding a polypeptide capable of specifically binding to a constant region of a virus nonstructural protein that is essential for propagation of said infecting virus, whereby the binding interferes with the activity of said nonstructural viral protein and inhibits the propagation of said virus, wherein said DNA sequence is operably linked to an RNA polymerase I promoter, a T3 RNA polymerase promoter or a T7 RNA polymerase promoter and is flanked by an RNA polymerase I transcription terminator, a T3 RNA polymerase transcription terminator or a T7 RNA transcription terminator sequence and by viral transcription and packaging signal sequences;

(ii) one or more plasmids comprising DNA sequences encoding said virus proteins that form a capsid; and (iii) one or more plasmids comprising DNA sequences encoding said virus membrane proteins;

whereby the virus proteins expressed by said plasmids of (ii) in said host cell form a capsid, and the intracellular transcription of the DNA of plasmid (i) generates a vRNA that is packaged within said capsid, which during the budding process acquires a portion of cell membrane lipids comprising the virus membrane proteins expressed by plasmids (iii), thus producing said virus-like particle, which are released from the host cell and may be further purified.

The number of expression plasmids comprising DNA sequences encoding said virus proteins is any number between 1 and the number of genes of said virus. However, since many of the viral gene products are responsible for the deleterious nature of viruses they are not used to produce the recombinant virus-like particle. In the example herein below, the capsid of the influenza-virus-like particle is encoded by 9 genes, each gene carried by a separate plasmid that are cotransfected into an eukaryotic cell. The invention may be performed having the 9 genes on less than 9 plasmids, for example, one plasmid comprising all 9 genes, or 2, 3, 4, 5, 6, 7 or 8 plasmids carrying the 9 genes divided between the plasmids. It is envisioned that additional viral genes may be found in the future to positively contribute to some aspect of the virus-like particle production process, and therefore the number of viral genes introduced into the host cell may be larger than 9.

Plasmids with capsid protein genes operably linked to an RNA polymerase I promoter may also be used to increase the vRNA gene numbers of said genes and thus increase efficiency of the virus-like particle production.

In certain embodiments, the method for producing a virus-like particle as defined above is directed to the production of an influenza A virus-like particle, wherein said DNA sequence of (i) is operably linked to an RNA polymerase I promoter and is flanked by an RNA polymerase I transcription terminator and by viral 3' and 5' UTR transcription and packaging signal sequences, and the DNA sequences of (ii) encode influenza A proteins and are operably linked to an RNA polymerase II promoter. In particular, the RNA polymerase I promoter is the human RNA polymerase I promoter represented by SEQ ID NO: 3, said RNA polymerase I transcription terminator sequence is of SEQ ID NO: 5 and said UTR sequences are represented by SEQ ID NO: 4 and SEQ ID NO: 6, and said influenza A virus proteins of (ii) are the PB1, PB2, PA, NP, M1, M2, and NS2 proteins, and of (iii) are hemagglutinin and neuraminidase.

In another aspect, the invention relates to a method of treating a viral infection, comprising administering to a subject infected with a virus an effective amount of a virus-like particle based on the same virus as defined above. In particular, the viral infection is influenza A infection and the virus-like particle is based on an influenza A virus. The propagation of the influenza A virus is inhibited because the protein inhibitor encoded by the vRNA of the influenza A virus-like particle interferes with the assembly of PB1, PB2 and PA into RDRP and thus inhibits transcription of the viral genome and the propagation of the virus.

Even if a few viruses are successfully assembled in an infected cell, the vRNA encoding the protein inhibitor is packaged within the viral particles in place of the original viral genomic material and thus, the virus becomes not only harmless, but also helpful in delivering the anti-viral gene to other cells.

In cases when the virus is an influenza A virus, this fact ensures that the virus-like particle would infect the same cell types as the naturally occurring influenza A virus upon which it is based. This is due to the presence of identical heamaglutinin sialic receptors on the virus-like particle and on the naturally occurring virus. The highly specific administration of the virus-like particles maximizes the safety of the use of these particles since tissue not infected by the naturally occurring virus are not affected by the virus-like particles. An additional beneficial effect gained by the fact that the virus-like particles are based on the naturally occurring influenza A virus is that the immune system of most humans have already experience an influenza infection, and thus the reaction of the immune-system to the virus-like particles is not expected to be deleterious to the treated person.

The invention is directed primarily to the treatment of subjects infected with a virus; however, prevention of the development of disease is also envisioned, for example, in case of an epidemic outbreak of influenza. The influenza virus-like particles may stay intact inside the cells of a subject for a period of several days, and the preventive treatment may prevent the infection to develop.

The invention also relates to a pharmaceutical composition comprising a virus-like particle as defined above and a pharmaceutically acceptable carrier, optionally with other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. Solid or liquid particulate virus-like particles prepared for practicing the present invention should include particles of respirable size: that is, particles of a size sufficiently small to pass through the mouth and larynx upon inhalation and into the bronchi and alveoli of the lungs. In general, particles ranging from about 1 to 5 microns in size (more particularly, less than about 4.7 microns in size) are respirable. Particles of non-respirable size which are included in the aerosol tend to be deposited in the throat and swallowed, and the quantity of non-respirable particles in the aerosol is preferably minimized For nasal administration, a particle size in the range of 10-500 µm is preferred to ensure retention in the nasal cavity. As an injection medium, it is preferred to use water that contains the additives usual for injection solutions, such as stabilizing agents, salts or saline, and/or buffers.

The route of administration of the pharmaceutical composition comprising the virus-like particles would be chosen to optimize the exposure of the infected tissue to the virus-like particles. For example, influenza A virus-like particles may be administered by inhalation of an aerosol comprising the virus-like particles in addition to an acceptable pharmaceutical carrier, thus directing the virus-like particles directly to the affected tissue. The invention will now be illustrated by the following non-limiting Examples.

EXAMPLES

Example 1

Selection of scFv Antibodies Specific for an Influenza A Non-Structural Protein

We used antibody phage display library (disclosed in Azriel-Rozenberg et al. 2004 and kindly provided by Dr Benhar, Tel Aviv University, Israel) for isolating scFvs against the influenza virus. In short, Benhar's group prepared the scFv repertoire comprising the library by amplification of antibody genes by PCR using human spleen, lymph node and peripheral blood lymphocyte cDNA as a template as described in Azriel-Rozenfeld et al. (2004). In this library, the repertoire of antibody (or scFv) genes is fused to the p3 gene of the m13 filamentous phage, and the fusion protein is then displayed on the phage surface.

In priniciple, to select for a specific antibody the antigen of interest is attached to magnetic beads and the phages expressing scFv on their surface are contacted with the beads. Phages binding specifically to the beads are isolated, used to transfect bacteria, and used in additional rounds of selection (panning) to amplify the frequency and affinity of the desired clones.

In this study, the antigen chosen was the 25 amino acid peptide of the amino acid sequence MDVNPTLLFLKV-PAQNAISTTFPYT (SEQ ID NO: 1), derived from the PB1 subunit of influenza A virus RDRP. This antigen was chosen because biochemical analyses have shown specific interactions between PB1 and PA as well as PB2, indicating that PB1 is the backbone of the complex. Forty-eight amino acids at the N terminus of PB1 were sufficient for binding PA in vivo, with the same efficiency as the complete PB 1 protein Another study mentions that the PA binding region on the PB1 was mapped within the 25 N-terminus amino acids of PB1. It was therefore hypothesized that an antibody binding to this peptide within the PB1 subunite would be capable of inhibiting the assembly of the RDRP complex.

Material and Methods

The techniques used herein are techniques commonly known to a person skilled in the art of preparation and use of phage display libraries and were as previoulsy published (Azriel-Rozenberg et al. 2004; Benhar and Reiter, 2001). In short, the following steps were perforemed to select for the desired antibodies:

An aliquot was taken from the stock of the phage display library (bacteria infected with phage) and helper phage M13K07 (5 µl/ml of $2 \times 10^{11}$ CFU/ml) was added to the bacterial culture to multiply the number of phages. Both phage and the streptavidin-coated magnetic beads (Dynal, Norway) were blocked with bovine serum albumin (BSA) to minimize non-specific binding. The phage were depleted of binders of irrelevant antigen by exposure of the phage to such antigen, binding to blocked beads and precipitation of the beads by exposing tubes to a magnet. The unbound phages (in the supernatant) were transferred to a fresh tube. Biotinylated antigen, the 25 amino acid PB1 antigen (SEQ ID NO: 1), was added to the depleted phages. Phages with bound antigen were then bound to the blocked beads. After washing, the phage was eluted with 100 mM triethylamine (TEA) buffer, pH 13. The neutralized eluate was used to infect bacteria that were grown on agar plates and used to produce phages for subsequent rounds of panning as described above.

Results. We isolated six scFvs that specifically bind to the 25 amino acid PB1 antigen of influenza A as can be seen by the differential binding to the PB1 peptide and BSA (FIG. 1). The gene encoding the scFv with the highest binding to this antigenic peptide (scFv #3 in FIG. 1) was seqeunced and this sequence is disclosed herein as SEQ ID NO: 2.

Example 2

Generation of Influenza A Viral Particles from Cloned cDNA

We have established a unique delivery system, which use the same virus that we want to inhibit as a vehicle to deliver the scFv. Our first "candidate" for inhibition is the Influenza A virus, hence the viral vector is based on the Influenza and prepared by reverse-genetics method.

We used a reverse-genetics system that allows us to efficiently generate influenza A viruses entirely from cloned cDNAs. Human embryonic kidney cells (293T) were co-transfected with nine expression vectors, each encoding a viral protein of the H1N1 strain (A/WSN/33) of influenza virus, as described in Neumann et al. (1999), and one plasmid encoding for the scFv. The nine expression vectors were obtained from Dr Kawaoka, Department of Pathobiological Sciences, School of Veterinary Medicine, University of Madison-Wisconsin, Wis., USA. Briefly, the cDNA of the viral genes were cloned into the plasmids operably linked to the RNA polymerase II promoter. The different plasmids are described in Table 1.

The pcDNA762, pcDNA774 and pcDNA787 vectors are derived from the pCDNA vector (Invitrogen, USA). The pEWSN-HA, pCAGGS-WSN-NP0/14, pCAGGSWNA15, pCAGGS-WSN-M1-2/1, pCA-NS2, pEP24c(M2) vectors are derived from the pcagg vector (Cabri; http://www.cabri.org).

The plasmids and transfection reagent were mixed, 2 ml of Trans IT LT-1 (Panvera, Madison, Wis.) per mg of DNA, incubated at room temperature for 45 min, and added to the cells. Six hours later, the DNA—transfection reagent mixture was replaced by cDMEM (GIBCO) containing 1% Penstrep and 10% FCS.

TABLE 1

Expression vectors used in transfection of the 293T cells

| Viral cDNA gene | Expression vector |
| --- | --- |
| hemaglutinin (HA) | pEWSN-HA |
| neuraminidase (NA) | pCAGGSWNA15 |
| PB1 | pcDNA774 |
| PB2 | pcDNA762 |
| PA | pcDNA787 |
| viral nucleoprotein (NP) | pCAGGS-WSN-NP0/14 |
| M1 | pCAGGS-WSN-M1-2/1 |
| M2 | pEP24c |
| NS2 | pCA-NS2 |

We cloned the scFv gene (SEQ ID NO: 2; antisence copy) into a plasmid (pHH21, originally described by Hoffmann, E. (1997) Ph.D. thesis, Justus-Liebig-University, Giessen, Germany and obtained from Andrew Pekosz, Departments of Molecular Microbiology and Pathology & Immunology, Washington University School of Medicine, St. Louis, Mo., USA) where the scFv is flanked by the human RNA polymerase I promoter (SEQ ID NO: 3) with a 5' untranscribed region (UTR; SEQ ID NO: 4) and the RNA polymerase I terminator (SEQ ID NO: 5) with a 3' UTR (SEQ ID NO: 6) (FIGS. 2A-B). Intracellular transcription of that construct by RNA polymerase I in 293T cells generated an scFv vRNA that was packaged into influenza virus-like particles.

The RNA polymerase I promoter was chosen to drive the expression of the scFv gene because it transcribes RNA without modifications (like addition of poly A). However, there are other promoters that could have been used equally well, such as T3 or T7 RNA polymerase with helper plasmid encoding the RNA polymerease.

In order to increase the expression level of the peptide inhibitor, the VLP is optionally generated with a DNA sequence that comprise 2, 3, 4, 5, 6, 7, 8, 9, 10, or more copies encoding for the polypeptide of SEQ ID NO: 1 or SEQ ID NO: 2. Each copy may be operably linked to a promoter and flanked by a terminator or the copies may be separated by nucleotide sequences encoding recognition sites for nucleases that produce RNA fragments that each encode for one polypeptide inhibitor, or recognition sites for proteases that cleave the polypeptide product into multiple copies of the desired inhibitor.

Example 3

Inhibition of Wild Type Influenza A Viral Replication in Cells Expressing scFv Specific for an Essential Non-Structural Viral Protein To test if the scFv expressed inside the infected cell inhibits the activity of the viral RDRP, the recombinant virus-like particles were mixed with a quantity of wild type virus that would produce a cytopathic effect in 50% of the cell cultures inoculated with the virus ($TCID_{50}$). We infected 293T cells with the mixture of wild type virus and virus-like particles or with wild type virus alone (control) by incubating the cells with the viruses and virus-like particles in 96 well plates at 37° C., 5% $CO_2$, for 3 days. Visual examination of cytopathic effect showed inhibition of viral propagation in cell cultures infected with the viruses and virus-like particle mixture as compared to the control.

Example 4

Inhibition of Wild Type Influenza A Viral Replication in Cells Expressing a RDRP Binding Peptide To show that the concept provided in the instant invention is a general concept, another molecule, the peptide of SEQ ID NO: 1 consisting of the first 25 amino acids of the PB1 terminus comprising the PA binding domain, was shown to inhibit interactions of influenza proteins with great efficiency.

The VLPs expressing this peptide were generated as described in Example 2 above, except that a sequence encoding for the scFv was replaced with a sequence encoding for the peptide of SEQ ID NO: 1.

Figure 3A:
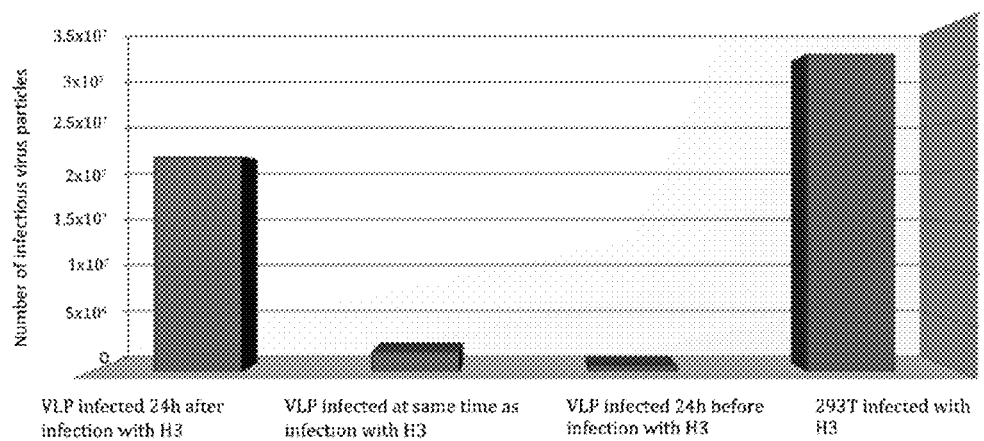
FIGS. 3A-3C show inhibition of Influenza $H_3N_2$ (H3) (A) or $H_1N_1$ (H1) (B) infectivity in human embryonic kidney (293T) cells and viability of the cells (C) after treatment with viral-like particles (VLP) expressing the PB1 peptide of SEQ ID NO: 1.
Figure 3B:
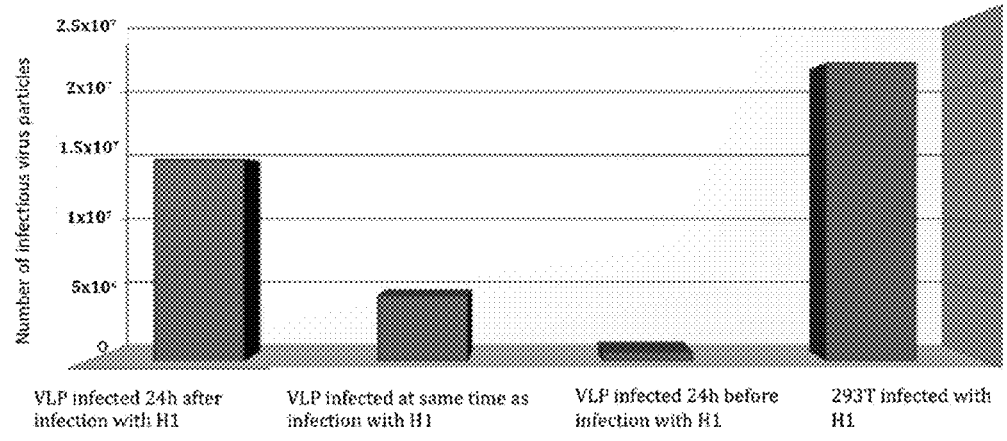
Figure 3C:
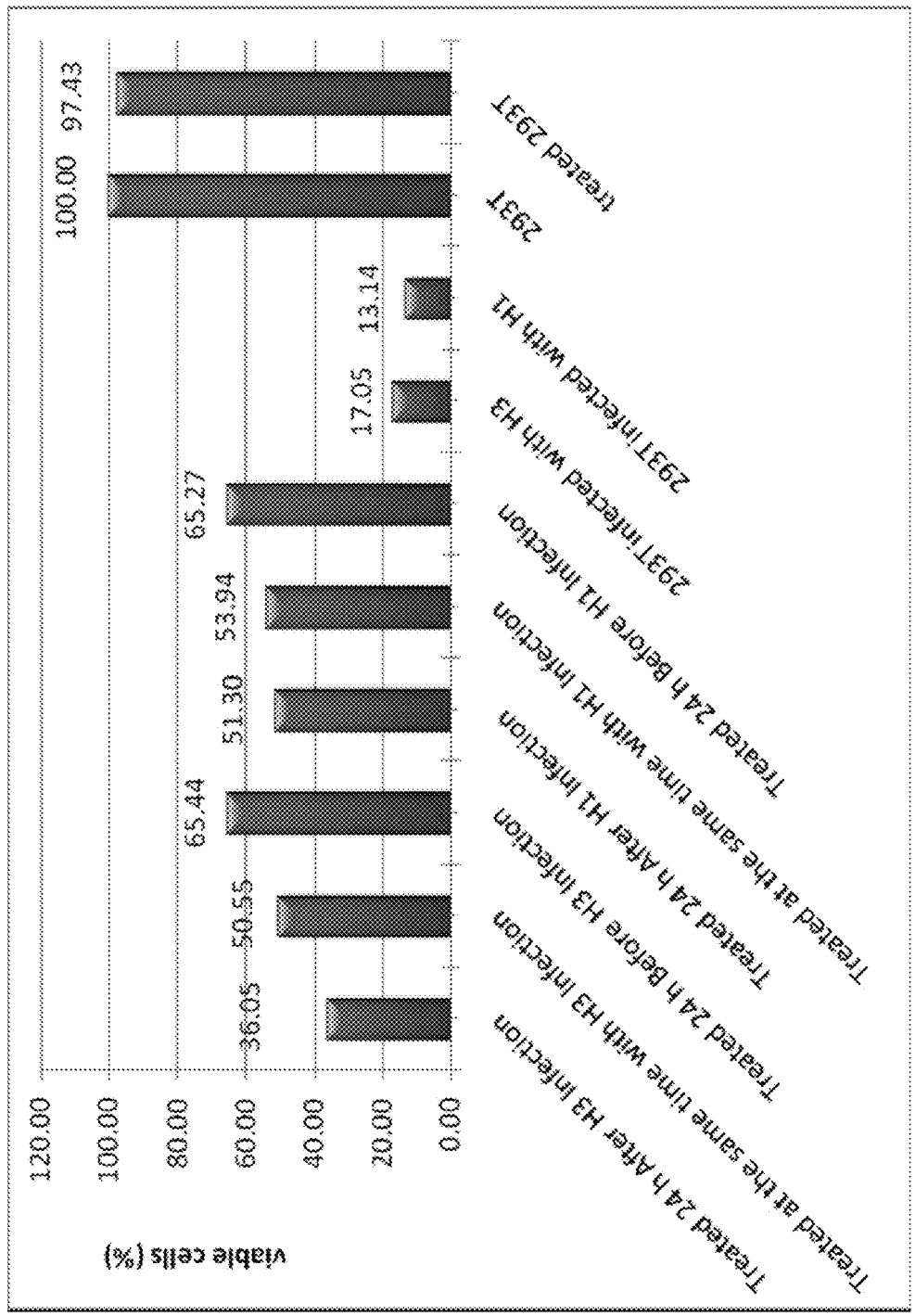

Thus, FIGS. 3A-B show that treatment of 293T cells with the PB1 terminus peptide expressing VLP inhibits $H_3N_2$ (FIG. 3A; H3) and $H_1N_1$ (FIG. 3B; H1) Influenza virus infection and improves the viability the infected cells (FIG. 3C).

Example 5

Inhibition of Wild Type Ebola Viral Replication

VLPs encoding for a scFv against a nonstructural protein that is essential for the propagation of Ebola virus is generated as explained in Example 2 above, and used to infect cells previously infected with wild type Ebola virus.

Tests are done as described above in Examples 3 and 4 to show that the expression of the scFv inhibits the propagation of the virus.

REFERENCES

Azriel-Rosenfeld, Ronit, Moran Valensi and Itai Benhar (2004). A Human Synthetic Combinatorial Library of Arrayable Single-chain Antibodies based on Shuffling in Vivo Formed CDRs into General Framework Regions J. Mol. Biol. 335: 177-192

Marks, J. D., Hoogenboom, H. R., Griffiths, A. D. & Winter, G. (1992) J. Biol. Chem. 267, 16007-16010

Neumann, G, Tokiko Watanabe, Hiroshi Ito, Shinji Watanabe, Hideo Goto, Peng Gao, Mark Hughes, Daniel r. Perez, Ruben Donis, Erich Hoffmann, Gerd Hobom, and Yoshihiro Kawaoka (1999) Generation of influenza a viruses entirely from cloned cDNAs. Proc. Natl. Acad. Sci. USA 96: 9345-9350

The invention claimed is:

1. A virus-like particle adapted for treating a viral infection, wherein said virus-like particle is based on an infecting virus causing the viral infection, with the proviso that said infecting virus is not a hepatitis C virus, and said virus-like particle comprises:

recombinant viral proteins which are of the same species as said infecting virus and form a capsid, recombinant viral membrane proteins which are of the same species as said infecting virus and are attached to the surface of said capsid, and vRNA packaged within said capsid, wherein said vRNA is generated by intracellular transcription of a DNA sequence encoding a polypeptide capable of specifically binding to a constant region of a nonstructural protein of said infecting virus, said nonstructural protein being essential for propagation of said infecting virus, whereby said binding interferes with the activity of said nonstructural viral protein and inhibits the propagation of said virus.

2. The virus-like particle according to claim 1, wherein said infecting virus is selected from the group consisting of an RNA negative sense virus, an RNA ambisense virus, and an RNA positive sense virus.

3. The virus-like particle according to claim 2, wherein said negative sense virus is selected from the group consisting of orthomyxoviridae, paramyxoviridae, filoviridae, rhabdoviridae, arenaviridae and bunyaviridae families of virus and said positive sense virus is a flaviviridae family of virus.

4. The virus-like particle according to claim 3, wherein said orthomyxoviridae virus is an influenza virus, said paramyxoviridae virus is human respiratory syncytial virus, said filoviridae virus is ebola virus or Marburg virus, said rhabdoviridae virus is rabies virus, said arenaviridae virus is lassa virus, said bunyaviridae virus is hanta virus.

5. The virus-like particle according to claim 4, wherein said virus is influenza A virus.

6. The virus-like particle according to claim 1, wherein said virus nonstructural protein is selected from the group consisting of:
the PB1, PB2, or PA subunit of the RNA dependent RNA polymerase (RDRP), the nucleoprotein (NP) or the M protein of an influenza virus;
the NP or RDRP of a human respiratory syncytial virus;
the L, VP35, NP, or VP30 protein of an ebola or Marburg virus;
the NP or RDRP protein of a rabies virus;
the L (RDRP) or N (Nucleoprotein) protein of a lassa virus; and
the L (RDRP) or N (Nucleoprotein) protein of a hanta virus.

7. The virus-like particle according to claim 6, wherein said nonstructural protein is selected from the group consisting of the PB1, PB2, and PA subunits of the RNA dependent RNA polymerase (RDRP), the nucleoprotein (NP), and the M protein of influenza virus.

8. The virus-like particle according to claim 6, wherein said virus nonstructural protein is involved in a cellular process essential for propagation of the virus selected from the group consisting of replication of the viral genetic material, packaging of said genetic material into the viral capsid and budding of the capsid from the host cell.

9. The virus-like particle according to claim 8, wherein said virus is influenza A virus, said cellular process is replication of the viral genetic material, and said nonstructural viral protein is the PB1 subunit of influenza A virus RDRP.

10. The virus-like particle according to claim 9, wherein said DNA sequence encodes (i) a single chain variable fragment antibody (ScFv) polypeptide capable of specifically binding to the PA binding domain of the PB1 subunit of the influenza A virus RDRP, or (ii) a peptide fragment comprising the N-terminal amino acid sequence of the PB1 subunit, which peptide fragment is capable of binding to the PB1 binding domain of the PA subunit so as to compete with the PB1 subunit of influenza A virus RDRP for binding to the PA subunit and inhibit viral propagation.

11. The virus-like particle according to claim 10, wherein said DNA sequence encodes a scFv polypeptide.

12. The virus-like particle according to claim 11, wherein said scFv polypeptide specifically binds to the PB1 N-terminus amino acid sequence of SEQ ID NO: 1.

13. The virus-like particle according to claim 12, wherein said scFv is encoded by a DNA sequence represented by SEQ ID NO: 2.

14. The virus-like particle according to claim 10, wherein said peptide fragment is represented by SEQ ID NO: 1.

15. The virus-like particle according to claim 1, wherein said recombinant virus membrane proteins are hemagglutinin and neuraminidase, and said vRNA is generated by intracellular transcription of the DNA sequence of an scFv.

16. A method for producing a virus-like particle according to claim 1, comprising introducing into an eukaryotic host cell:
(i) a plasmid comprising a DNA sequence encoding a polypeptide capable of specifically binding to a constant region of a virus nonstructural protein that is essential for propagation of said infecting virus, whereby the binding interferes with the activity of said nonstructural viral protein and inhibits the propagation of said virus, wherein said DNA sequence is operably linked to a promoter selected from the group consisting of an RNA polymerase I promoter, a T3 RNA polymerase promoter and a T7 RNA polymerase promoter and is flanked by a terminator selected from the group consisting of an RNA polymerase I transcription terminator, a T3 RNA polymerase transcription terminator and a T7 RNA transcription terminator sequence and by viral transcription and packaging signal sequences;
(ii) one or more plasmids comprising DNA sequences encoding said virus proteins that form a capsid; and
(iii) one or more plasmids comprising DNA sequences encoding said virus membrane proteins;
whereby the virus proteins expressed by said plasmids (ii) in said host cell form a capsid, and the intracellular transcription of the DNA of plasmid (i) generates a vRNA that is packaged within said capsid, which during the budding process acquires cell membrane lipids along with the virus membrane proteins expressed by plasmids (iii), thus producing said virus-like particle, which are released from the host cell.

17. A pharmaceutical composition comprising the virus-like particle of claim 1 and a pharmaceutically acceptable carrier.

18. A virus-like particle according to claim 1, wherein said vRNA contains a sequence encoding a polypeptide capable of specifically binding to a constant region of a nonstructural protein of said infecting virus instead of containing the genetic material of the wild-type virus.

* * * * *